United States Patent [19]
Hinton

[11] Patent Number: 5,817,225
[45] Date of Patent: Oct. 6, 1998

[54] ELECTROPHORESIS SYSTEM FOR THE PURIFICATION, CONCENTRATION AND SIZE FRACTIONATION OF NUCLEIC ACIDS

[75] Inventor: Stephen M. Hinton, Chester, N.J.

[73] Assignee: Exxon Research and Engineering Company, Florham Park, N.J.

[21] Appl. No.: 968,836

[22] Filed: Oct. 10, 1997

Related U.S. Application Data

[63] Continuation of Ser. No. 698,618, Aug. 16, 1996, abandoned.

[51] Int. Cl.⁶ .................................................... G01N 27/26
[52] U.S. Cl. ............................................ 204/645; 204/468
[58] Field of Search ..................................... 204/451, 452, 204/455, 456, 466, 468, 549, 606, 605, 616, 645

*Primary Examiner*—Robert J. Warden
*Assistant Examiner*—Alex Noguerola
*Attorney, Agent, or Firm*—Ronald D. Hantman

[57] ABSTRACT

The present invention is an electrophoretic unit for the purification, concentration, and size fractionation of nucleic acids contaminated by organic acids, such as humic acids. The electrophoretic unit includes a counter ion, Bis (2-hydroxyethyl)-imino-tris (hydroxymethyl)-methane (BisTris), and an electrolyte 2-(N-Morpholino) ethanesulfonic Acid (MES).

5 Claims, 1 Drawing Sheet

CATHODE CHAMBER     SEPARATION CHAMBER     ANODE CHAMBER

CATHODE CHAMBER     SEPARATION CHAMBER     ANODE CHAMBER

ELECTROPHORESIS SYSTEM FOR THE PURIFICATION, CONCENTRATION AND SIZE FRACTIONATION OF NUCLEIC ACIDS

This is a continuation of application Ser. No. 698,618, filed Aug. 16, 1996, now abandoned.

BACKGROUND OF THE INVENTION

The present invention relates to electrophoresis. In particular, it relates to the electrophoretic separation of nucleic acids from organic acids. The primal technical hurdle in the application of molecular technology for environmental studies is the recovery and purification of nucleic acids in a quality and quantity required for molecular genetic analysis. An idealized technology for isolating nucleic acids from an environmental sample would be a quantitative recovery of concentrated DNA that has been purified from any components interfering with subsequent analyses. For example, most soils, sediments, or plant material have humic acids which are formed during the degradation of plant matter. Humic acids with phenolic groups oxidize to form quinones that covalently bond to DNA and proteins. Humic acids have been shown to be the principle denaturant of proteins, i.e. enzymes used to perform recombinant DNA reaction, therefore humic acids must be removed from DNA extracts before such analyses. This report describes the development of an electrophoresis technology that separates nucleic acids and humic acids yielding concentrated, high quality DNA which solves a key technical hurdle in the application of molecular techniques for environmental sciences.

The multiphasic electrophoresis technology described in this invention is based upon a strategy that takes advantage of the difference in the electrophoretic mobility of nucleic acids and humic acids. The term multiphasic electrophoresis describes a buffer system that has more than one electrophoretic principle operating in the gel support medium. The multiphasic system exploits the concentration and purification power of isotachophoresis in combination with the separation power of zone electrophoresis.

In zone electrophoresis ions to be separated are in a homogenous buffer and are moving in the electric field at different velocities. In isotachophoresis, a steady-state configuration is achieved when all ions move with equal (iso) velocities (tacho), and the ions are aligned one after another according to their effective mobilities. The effective mobility of an ion depends on charge, viscosity, molecular size and shape, solvation, dielectric constants, and temperature. For partly ionized molecules, like nucleic acids, the degree of ionization is another parameter influencing mobility, because ions are electrophoretically transported only in their charged state. For an anionic system, the anion becomes more negatively charged with increasing pH until at a high pH the maximum mobility is achieved. As a general rule, biological molecules are anionic and electrophoretically mobile at one pH unit above their isoelectric point, and the relative charge and effective mobility are roughly proportional. Consequently, the effective mobility of a molecule is dependent upon the pH of the buffer system. Therefore, the buffer system is composed of the "mobile" ion, i.e. acetate, bicine, MES, and nucleic acids, and a common counter ion that has buffering capacity which stabilizes the pH throughout the separation zones.

Under the isotachophoretic condition all ions are separated into discrete zones forming boundaries between each ion, the moving boundary principle. An electrophoretic separation by the moving boundary principle is described by the Kohlrausch regulating function (Everearts, F. M., Beckers, J. L., and T. P. E. M. Verhegeen. Isotachophoresis: Theory, instrumentation and applications. Elsevier, Amsterdam (1976)). The ion with the greatest effective mobility is the leading ion and the terminating constituent ions trail in order of descending effective mobility. The Kohlrausch regulating function describes the condition at steady-state when the concentration of charge in the leading ion zone determines the concentration of charges in all trailing zones. Therefore, under a standard set of conditions the zone length is proportional to concentration of the constituent in an electrophoresis apparatus with a compartment of uniform dimensions.

In the practical application of isotachophoretic separation, sample ions are introduced between the leading electrolyte, an ion with the highest mobility, and the terminating electrolyte, an ion with a lower mobility than that of any of the sample ions. The sample ions undergo a considerable concentration and sharpening between the leading and terminating ions. In contrast, the multiphasic system described in this invention takes advantage of isotachophoresis as a separation tool by the introduction of the spacer ion technique. Spacer ions have an intermediate-mobility forcing two consecutive ions of interest apart from one another. A multiphase buffer system introduces (2[N-morpholino] ethanesulfonic acid) (MES) as spacer ion in the environmental DNA sample making it possible to detect and purify humic acids and nucleic acids.

SUMMARY OF THE INVENTION

The present invention is an electrophoretic unit for the purification, concentration, and size fractionation of nucleic acids contaminated by organic acids, such as humic acids. The electrophoresis unit has an anode compartment including an anolyte having a leading ion, a cathode compartment including a catholyte having a terminating ion, and a separation chamber for the separation of nucleic acids and organic acids. The anolyte and catholyte are chosen such that the mobility of the nucleic acids are greater than the mobility of the terminating ion of the catholyte and the mobility of the organic acids are less than the mobility of the leading ion of the anolyte. The separation chamber includes an electrolyte with an ion whose mobility is between the mobilities of nucleic acids and organic acids. The electrolyte includes the same counter-ion.

In a preferred embodiment, the electrophoretic unit, referred to as multiphasic agarose gel electrophoresis, is composed of a counter ion, Bis (2hydroxyethyl)-imino-tris (hydroxymethyl)-methane (BisTris), that establishes and stabilizes the pH, several ions with successive electrophoretic mobilities and a support medium. At equilibrium, the ions are arranged in order of their electrophoretic mobilities creating boundaries between each ion zone. One of the ions, 2-(N-Morpholino)ethanesulfonic Acid (MES), has an intermediate electrophoretic mobility which separates, thereby purification of, nucleic and all other organic acids. The nucleic acids, and organic acids are concentrated between two different ion boundaries with MES as the common boundary ion. The separation and concentration process can be visually monitored by the addition of the dye, xylene cyanol (XC), which comigrates with nucleic acids. The nucleic acids can be recovered from the support medium, i.e., agaraose, in a pure and concentrated form which allows subsequent analyses without interference from contaminating organic acids.

DESCRIPTION OF PREFERRED EMBODIMENT

Figure 1:
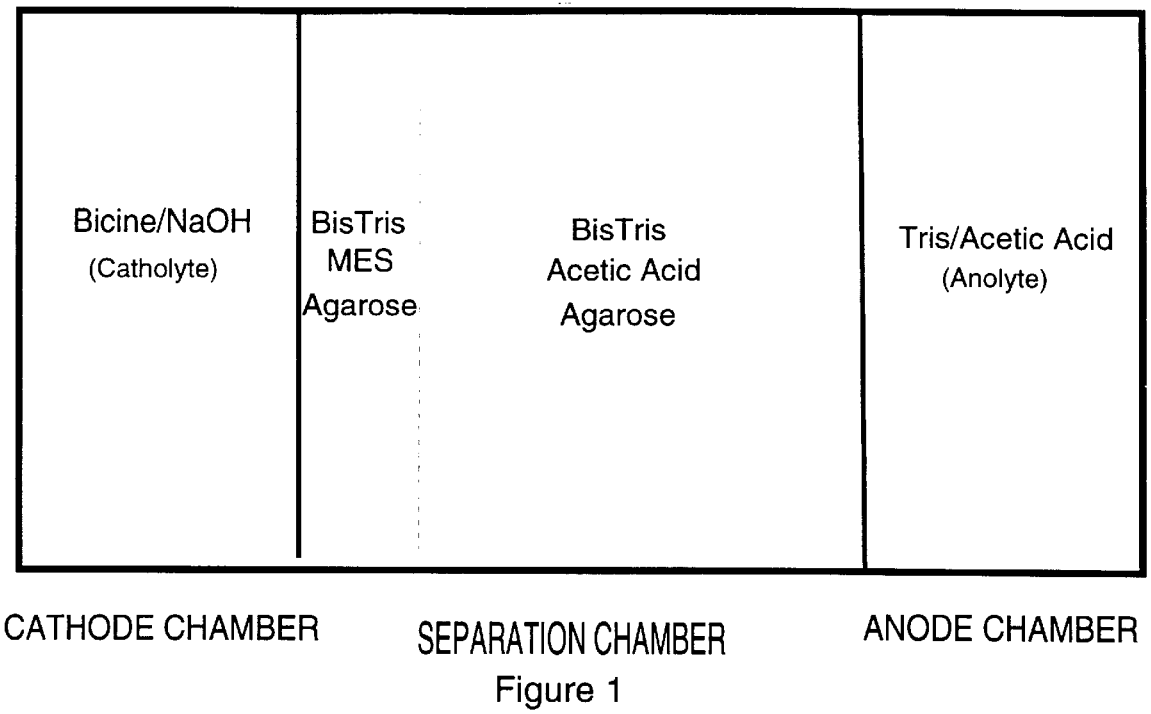
FIG. 1 shows a schematic diagram of the electrophoresis unit used for purification and concentration of environmental nucleic acids.

The invention requires a sample including DNA and organic acids to be separated.

DNA extraction methods from soils, sediments or plants require further steps to purify the DNA from co-extracted humic acids which interefere with subsequent molecular analyses. A multiphasic buffer system for (agarose gel) electrophoresis has been developed for the purification (and concentration) of environmental DNA from organic acids. The electrophoretic principle used is moving boundary electrophoresis (also referred to as isotachophoresis) which separates nucleic and organic acids due to differences in their effective electrophoretic mobilities. The buffer support medium can be agarose conventionally used to separate DNA by size. In contrast, the multiphasic technique uses agarose or any other support medium with a low molecular sieving capacity, FastLane agarose, FMC Corp, to stabilize the multiple buffer zones and not serve as a molecular sieve.

The multiple buffer zones have a common counter ion, BisTris (pKa=6.5 at 20° C.), that establishes and stabilizes the pH. The mobile ions are arranged in the agarose gel in the order of their electrophoretic mobilities with acetate (pKa=4.76 at 20° C.) being the leading ion, and N,N-bis (2hydroxyethyl)glycine (BICINE, pKa=8.35 at 20° C.) serving as the slowest or terminating ion. The environmental extract containing nucleic and humic acids are introduced in an agarose sample zone between the leading and terminating ions. MES (pKa=6.15 at 20° C.) which has an intermediate mobility between nucleic and organic acids is also included in the (agarose) sample zone in order to physically separate and isolate the extracted acids. The distance the nucleic and organic acids are separated is proportional to the concentration of MES due to the moving boundary regulating function. The (Kohlrausch) regulating function states that at steady-state the concentration of charge in the leading ion zone determines the concentration of charges in all trailing zones. Therefore, at a constant pH increasing the amount of MES by increasing its concentration or the size of the sample zone adjusts the distance proportionally between the nucleic and organic acids.

The addition of xylene cyanol dye (XC) to the sample allows the experimenter to visually monitor the separation process. Initially, the nucleic acids (and XC) have a slower mobility than other sample ions until they are concentrated between the (BICINE) terminating and (MES) spacer ions. On the other hand, the extracted organic acids migrate to the boundary between the (MES) spacer and (acetate) leading ions. At this point the system is in equilibrium with all ions moving at equal velocity, hence the name isotachophoresis. The ionic strength (0.1M mobile ions) of the buffer system as been adjusted so the nucleic acids greater than 700 basepairs (bp) comigrate with XC revealing their location in the agarose. While translumination of the agarose at 300 nm without ethidium bromide reveals the humic acids as a "blue" band migrating in front of the DNA/XC band approximately the distance of the sample gel width. DNA fragments less than 700 bp but greater than 400 bp migrate in the spacer zone while fragments less than 400 bp comigrate with humic acids. This adjustment of the buffer system to exclude small DNA fragments (<700 bp) from the DNA/XC zone is important for Polymerase Chain Reaction (PCR) amplification. Small DNA (or RNA) fragments can serve as "false" primers reducing the yield of PCR amplification, and producing spurious products.

Thus, a novel multiphasic buffer system for agarose gel electrophoresis is disclosed that can be used to purify and concentrate eDNA from multiple (100s) environmental samples conveniently and rapidly which is required for the application of molecular techniques. Multiphasic (agarose) electrophoresis at equilibrium concentrates the environmental deoxyribonucleic acids (eDNA) in one buffer boundary and the humic acids in a second buffer boundary which are separated by the spacer ion, 2-(N-Morpholino) ethanesulfonic Acid (MES). The use of xylene cyanol dye allows the experimenter to determine when the separation is complete and the exact location of the nucleic acids in the agarose gel. Following the completion of the separation technique, the purified environmental DNA in the support medium can be easily recovered for PCR amplification or directly blotted onto a membrane for molecular probing.

Multiphasic Agarose Gel Electrophoresis

The electrophoresis system can be performed in two configurations to achieve either of the following:

1. Purification and Concentration of Environmental Nucleic Acids

The multiphasic agarose gel buffer system for the concentration and purification of nucleic acids extracted from an environmental sample is cast in two stages. First, the stacking gel (0.4M BisTris, 0.1M Acetic acid and 1% (W/N) FastLane Agarose, FMC Corp., Maine) is cast by pouring the molten agarose (at 55° C.) into the electrophoresis chamber to a thickness of approximately 1 cm. After the stacking gel has solidified, using a straight-edge as a guide for a scalpel, approximately 1 cm of the stacking gel on the end the sample comb will be inserted is first cut then removed. This portion of the gel that has been removed provides the chamber for casting the sample gel. The molten sample gel (0.4M BisTris, 0.1M MES, and 1% (W/V) FastLane Agarose) is poured into the 1 cm mold with the sample comb positioned in place so that the sample wells will be as close as possible to the catholyte chamber (see FIG. 1).

Figure 2:
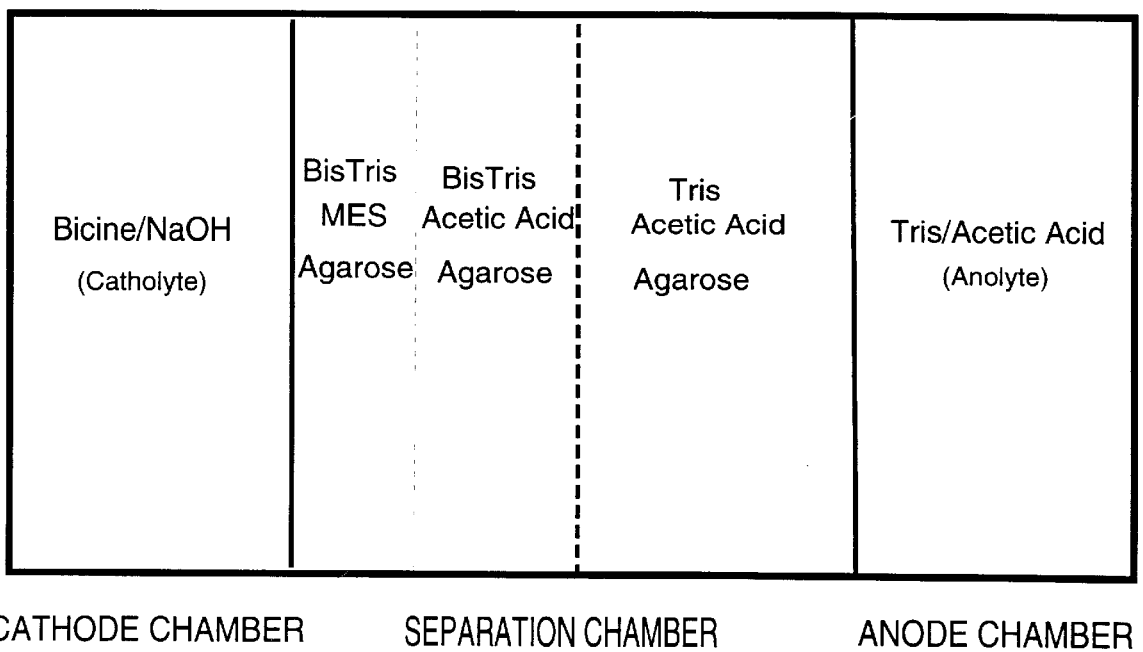
FIG. 2 shows a schematic diagram of the electrophoresis unit used for purification, concentration and size separation of environmental nucleic acids.

2. Purification, Concentration and Size Separation of Environmental Nucleic Acids The multiphasic agarose gel buffer system for the concentration, purification, and size separation of nucleic acids requires an additional casting of the separation gel. First the separation gel (0.4M (Tris)Hydroxymethyl)Amino Methane)(Tris), 0.1M Acetic Acid and SeaKem GTG agarose, FMC Corp., Maine) is cast in the electrophoresis chamber then approximately 3 cm of the solidified gel is removed as described above. The stacking and sample gel are cast in the vacant space as described. Please note that the stacking gel width must be at least twice the width of the sample gel for the buffer system to achieve equilibrium (see FIG. 2).

The multiple buffer zones or phases must be discrete, therefore, if a gel casting tray is used silicone grease is applied to the outside of the tray in order to prevent the catholyte and anolyte from mixing. The catholyte (0.2M Bicine and 0.1N NaOH) is added on the side of the gel with the sample wells up to but not over the top edge of the gel, likewise, the anolyte is added to its chamber. Please note that this modification of the conventional "submarine gel" configuration results in a "seal level gel" technique.

The extracted environmental nucleic acid were resuspended in sample buffer containing the tracking dye (0.1% (W/V) xylene cyanol in 0.4M BisTris and 0.1M MES). The samples are loaded into the wells and a constant current of 10 milliamps/cm2 of the end of the agarose gel (for example, a gel 1 cm thick and 5 cm wide has a 5 cm2 end dimension; 5 cm2×10 mA/cm2=50 mA, therefore, the electrophoresis requires 50 mA of constant current). The multiphasic buffer system will have come to equilibrium, which concentrates and purifies the eDNA, when the Xylene Cyanol "tracking" dye has migrated 2 cm into the stacking gel. A general rule is the sample (Xylene Cyanol) must migrate into the stacking gel twice the distance of the width of the sample gel to achieve equilibrium.

What is claimed is:

1. An electrophoresis unit comprising an anode compartment including an anolyte having a leading ion, a cathode compartment including a catholyte having a terminating ions, a separation chamber, a mixture of nucleic acids and organic acids in said separation chamber wherein the mobility of said nucleic acids are greater than the mobility of the terminating ion of said catholyte and the mobility of said organic acids are less than the mobility of the leading ion of said anolyte, and an electrolyte in said separation chamber whose electrophoretic mobility is between the mobilities of the nucleic acids and organic acids of said mixture and wherein said electrolyte includes the same counter-ion through out the separation chamber, and 2-(N-Morpholino) ethanesulfonic Acid (MES).

2. The electrophoresis unit of claim 1 wherein said electrolyte includes the counter ion bis(2-hydroxyethyl) imino-tris(hydroxymethyl)-methane (BisTris).

3. The electrophoresis unit of claim 2 wherein said separation chamber includes a counter ion that is more basic than BisTris.

4. The electrophoresis unit of claim 1 wherein said leading ion is acetate and said terminating ion is N,N-bis (2-hydroxyethyl)glycine (BICINE).

5. The electrophoresis unit of claim 1 further comprising xylene cyanol dye in said mixture of nucleic acids and organic acids.

* * * * *